United States Patent [19]

Kamimae et al.

[11] 4,410,541
[45] Oct. 18, 1983

[54] COMPOSITE FOR IMPROVING LIPID METABOLISM

[75] Inventors: Hiroshi Kamimae, Yokohama; Tadashi Ishikawa, Sagamihara, both of Japan

[73] Assignee: Nihon Nosan Kogyo K.K., Yokohama, Japan

[21] Appl. No.: 351,177

[22] Filed: Feb. 22, 1982

[30] Foreign Application Priority Data

Mar. 2, 1981 [JP] Japan ............................. 56-028482

[51] Int. Cl.³ ..................................... A61K 31/415
[52] U.S. Cl. ................................ 424/273 R; 548/342
[58] Field of Search .................... 548/342; 424/273 R

[56] References Cited

PUBLICATIONS

*Chemical Abstracts*, 93:137,984p (1980) [Japan. Kokai 79, 160,741, Ishikawa et al., 12/19/79].

*Chemical Abstracts*, 89:22749r (1978) [Japan. Kokai 78, 24,065, Ishikawa et al., 3/6/78].

*Chemical Abstracts*, 94:44383x (1981) [Imai, Kitakanto Igaku 1979, 29(5), 303–321].

*Chemical Abstracts*, 94:44396d (1981) [Imai, K. et al., Thyroid Res. 8, Proc. Int. Thyroid Congr., 8th, 1980, 248–251].

*Primary Examiner*—Richard A. Schwartz
*Attorney, Agent, or Firm*—Martin Smolowitz

[57] ABSTRACT

A composite has an effect of improving lipid metabolism. The effective component of the composite is monoiodohistidine. Monoiodohistidine may be obtained by a biological process, which comprises adding an iodine compound and/or a seaweed to a feed for egg-laying birds, and feeding the feed to the egg-laying birds so that eggs of the birds contains a high amount of monoiodohistidine.

3 Claims, No Drawings

COMPOSITE FOR IMPROVING LIPID METABOLISM

DESCRIPTION

This invention relates to a composite having an effect of improving lipid metabolism.

An object of the present invention is to provide cheaply the composite which can be used with safety and without any side effect, the effect of improving lipid metabolism being represented as an effect of heightening a constitution ratio of high-density lipoprotein (HDL) in the blood, as an effect of decreasing plasma triglyceride, as an effect of heightening lipoprotein lipase activity, as an effect of decreasing amount of whole haematic cholesterol, and as an effect of treating diabetes with promoting insulin secretion.

It is known that iodine is a requisite component for thyroid hormone, and iodine agent is used mainly for thyroid gland diseases. It is also reported that iodine agent may be used for ophthalmic diseases, infantile diseases such as bronchial asthma, cholesterol removal, obstetric and gynecologic diseases, fungous diseases and so on. The iodine agent is usually dosed in the form of potassium iodide, sodium iodide or Lugol's solution. However, dosing of such iodide is not desirable, because it tends to cause iodo-rash, iodo-catarrh, gastroenteric trouble and so on, and because iodine agent itself tends to change in quality.

Under such situation, inventors of the present invention have conducted many studies on iodine compounds and their useful quality. As the result of such studies, the inventors have found that monoiodohistidine has an effect of improving lipid metabolism, more particularly, of heightening constitution ratio of high-density haematic lipoprotein, of decreasing plasma triglyceride, of heightening lipoprotein lipase activity, of decreasing amount of whole haematic cholesterol, and of treating diabetes by promoting insulin secretion, and completed the present invention thereby.

The effective component of the composite of the present invention is monoiodohistidine. In general, monoiodohistidine may be produced by a synthesizing process, which comprises dissolving histidine hydrochloride in sodium hydroxide solution, and causing to react with an iodine compound under cooled condition. On the other hand, monoiodohistidine which can be used with safety and without side effect is easily and cheaply obtained by the following biological process.

The present process comprises adding an iodine compound, a seaweed and/or a processed seaweed to a feed for egg-laying birds in excess of an ordinary iodine requirement of them, and feeding the egg-laying birds with the feed so that a high amount of iodine contained in the feed is transferred to eggs which the egg-laying birds lay, and thereby the monoiodohistidine content of egg is increased. The iodine compound to be added is, for example, calcium iodate, potassium iodate, potassium iodide, sodium iodide, cuprous iodide, thymol iodide, calcium iodobehemate, diiodo salicylic acid and calcium periodate. The seaweed to be used is, for example, wakame and kombu. Considering health of egg-laying birds and an effect of increasing the monoiodohistidine content, the most desirable iodine compound is calcium iodate, and it is still more desirable to use calcium iodate and the seaweed jointly. The egg-laying birds to be used is, for example, a hen, a duck, a quail, a bantam and a guinea fowl.

Thus, at about a week after beginning to feed egg-laying birds with the feed containing much iodine, the egg-laying birds began to lay eggs containing a high amount of monoiodohistidine, that is to say, monoiodohistidine-enriched egg. For example, where egg-laying hens are fed with a feed containing about 50 ppm of iodine, they lay eggs containing about 250 $\mu$g of monoiodohistidine per egg. Where they are fed with a feed containing about 100 ppm of iodine, they lay eggs containing about 600 to 800 $\mu$g of monoiodohistidine per egg. And, where they are fed with a feed containing about 2,500 ppm of iodine, they lay eggs containing about 2,500 to 3,500 $\mu$g of monoiodohistidine per egg.

Although the monoiodohistidine-enriched egg may be used as the composite of the present invention as a whole, the yolk alone may be used as the present composite, because most of monoiodohistidine is contained in the yolk. The yolk may also be used after removing unnecessary portions or components therefrom. Means for removing unnecessary components from the yolk is, for example, concentration, acidization, extraction, dialysis, ultrafiltration, reverse infiltration, and ion-exchange, which are used alone or used in combination. Although the above eggs may be used in their natural or non-processed form, they also may be used in the form of granule, essence, tablet or powdered medicines by using various mass or bonding agents.

It is desirable to dose or ingest the present composite everyday so that the monoiodohistidine amount is 200 to 2,000 $\mu$g per day. And, the present composite is preferably dosed for a month or more, because it does not have an immediate effect but a slow effect.

The present composite for improving lipid metabolism has no side effect, and is excellent especially in improving constitution ratio of haematic high-density lipoprotein, in decreasing plasma triglyceride, in heightening lipoprotein lipase activity, and in decreasing the amount of haematic cholesterol. In addition, the present composite is effective against asthma, hyperpiesia, hypotension, allergic rhinitis, allergic dermatitis, anemia, diabetes, gout, constipation, nephritis, gastroenteric trouble and so on. It is also ascertained that an allergy to eggs may not be caused by the present composite, even if the composite is made of the whole egg, the yolk or processed egg or yolk.

The results of an acute virulence test of the composite is summarized as follows:

Acute Virulence Test

| Animals used: | Rats, Wistar descent | Sex: | Female |
|---|---|---|---|
| Body Weight: | 100 to 110 g | Number: | 10 heads |

The composite was dosed to the rats at a dosage increased in glometric ratio to the maximum of 100 g of monoiodohistidine per kg of body weight, and then the rats were observed after seven days. In the result, none of the rats died, and dissection showed that there was no abnormal change in the histology or tissue of rats. Thus, the composite was proved not to have any acute virulence.

Then, animals and clinical experiments were done as to the effect of improving lipid metabolism. The results of them are as follows:

Animal Experiment 1

Twenty heads of male rats of SD descent and three weeks old were fed in a voluntary running cage with a marketed solid base feed for rats for ten days, and thereafter the solid base feed was replaced with a powdered base feed made by Nihon Nosan Kogyo K.K. At the stage of seven weeks old, they were divided into a test group of the ten heads and a control group of ten heads so that the groups may be equally balanced in the body weight and voluntary running amount. The test group was fed with a test feed prepared by adding 1% of the composite containing 266 ppm of monoiodohistidine to the above powdered base feed, which the composite was obtained in the example 2 mentioned later. On the other hand, the control group was fed with a control feed prepared by adding 1% of powdered ordinary egg to the above powdered base feed. The test and control groups were fed with the respective feed for ten weeks at $25\pm2°$ C. of temperature and at 50 to 80% of humidity, and thereafter they were slaughtered by cutting heads. Then, the amount of whole haematic cholesterol (A) and the amount of hematic high-density lipoprotein cholesterol (B) were measured, and constitution ratio of haematic high-density lipoprotein (HDL Ratio =B/A) was calculated with the measured amounts.

The present composite was proved to have the effect of improving constitution ratio of haematic high-density lipoprotein, as shown in Table 1.

TABLE 1

| | Amount of whole cholesterol (A) (mg/dl) | Amount of HDL (B) (mg/dl) | Ratio of HDL (B/A) (%) |
|---|---|---|---|
| Test Group | 79.7 | 65.3 | 81.9 |
| Control Group | 82.8 | 64.4 | 77.7 |

In addition, activity of lipoprotein lipase (LPL) was measured as to the rats of the test and control groups.

The present composite was proved also to have the effect of heightening lipoprotein lipase activity, as shown in Table 2.

TABLE 2

| | ($\mu$ mole FFA/hr/wet. g) | |
|---|---|---|
| | LPL Activity in Adipose Tissue | LPL Activity in Skeletal Muscles |
| Test Group | 25.9 | 26.8 |
| Control Group | 21.4 | 21.6 |

*Enzymatic reaction was done by Gasquet's method, and the amount of isolated fatty acid was then determined by Dole's method as improved with Trout et al.

Animal Experiment 2

A test groups consisted of ten heads of male rats of Wistar descent, which weighed about 120 g. The test group was fed in a cage at $24\pm1°$ C. of temperature and at 50 to 60% of humidity. A feed containing 15% of cholesterol was fed to the rats for five days so that they got hypercholesterolemia. The composite to be tested was made from the yolk of egg of the egg-laying hens to which calcium iodate was fed. The composite was dissolved in distilled water, and then orally dosed to the rats by means of a stomach probe at the rate of 75 $\mu$g of monoiodohistidine per day per rat for five days in parallel with feeding of the cholesterol containing feed. The rats were caused to fast for a night after composite dosing was finished, and next morning blood was taken from fundus of the rat's eyes in order to measure the amount of whole cholesterol by Zurkowski's method.

A control group, a contrast group (1) and a contrast group (2) equally consisted of rats which got hypercholesterolemia by the same process as mentioned in the test group. While potassium iodide was dosed to the contrast group (1) so that the iodine amount would be equal to that of the test group, iodo-lecithin was dosed to the contrast group (2) so that the iodine amount would be equal to that of the test group. On the other hand, no iodine agent or compound was dosed to the control group. And, as to the rats of these groups, the amount of whole cholesterol was measured by the same method as mentioned in the test group.

The present composite was proved to have the effect of decreasing the amount of whole cholesterol, as shown in Table 3.

TABLE 3

| | Amount of whole Cholesterol (mg/dl) |
|---|---|
| Control group | 335 |
| Test group | 273 |
| Contrast Group (1) | 323 |
| Contrast Group (2) | 325 |

Clinical Experiment 1

Thirteen adult persons ingested ordinary eggs for two weeks at the rate of three eggs per day, and thereafter they ingested eggs containing on the average 650 $\mu$g of monoiodohistidine per egg for three weeks at the rate of three eggs per day, and then haemetic high-density lipoprotein (HDL) cholesterol was measured. The present composite was proved also to have the effect of increasing the amount of haematic high-density lipoprotein cholesterol, as shown in Table 4.

TABLE 4

| | HDL Cholesterol (mg %) |
|---|---|
| Before ingesting ordinary eggs | 44.5 |
| 2 weeks after ingesting ordinary eggs | 42.4 |
| 2 weeks after ingesting the composite | 48.3 |
| 3 weeks after ingesting the composite | 50.3 |

Clinical Experiment 2

The composite of the example mentioned later was dosed for three months to a number of patients who respectively got other diseases such as hyperpiesia, hypotension, anemia, diabetes and so on.

The composite was proved further to have the effect of improving or treating such diseases, as shown in Table 5.

TABLE 5

| Diseases | Patients Improved | Patients never Improved | Ratio of Improvement (%) |
|---|---|---|---|
| Asthma | 110 | 33 | 77 |
| Allergic rhinitis | 92 | 54 | 63 |
| Allergic dermatitis | 125 | 87 | 59 |
| Hyperpiesia | 267 | 71 | 79 |
| Hypotension | 105 | 43 | 71 |
| Anemia | 159 | 35 | 82 |

TABLE 5-continued

| Diseases | Patients Improved | Patients never Improved | Ratio of Improvement (%) |
|---|---|---|---|
| Diabetes | 52 | 9 | 85 |
| Gout | 24 | 8 | 75 |
| Constipation | 210 | 77 | 73 |
| Gastroenteric trouble | 302 | 62 | 83 |
| Nephritis | 37 | 9 | 80 |

EXAMPLE 1

Calcium iodate was added to a marketed feed for hens so that the iodine content became 100 ppm, and then the feed was fed to hens which had begun to lay eggs four months ago. Thus, seven days after the feeding, the hens laid eggs containing on the average 750 μg of monoiodohistidine per egg. The eggs were used as the composite of the present invention.

EXAMPLE 2

Calcium iodate was added to a marketed feed for hens so that the iodine content became 2,500 ppm, and powdered kombu (seaweed) was further added to the feed by 1%. The feed was fed to 200 heads of hens which had begun to lay eggs six months ago. The eggs obtained by the above feeding were broken, and divided into the yolk and the albumen.

Dextrin of 12.5 kg and a sufficient quantity of water were added to the yolk of 100 kg, and the admixture was dried by a spray-dryer. The composite obtained in such way contained monoiodohistidine of 266 mg/kg.

EXAMPLE 3

Calcium iodate was added to a marketed feed for hens so that the iodine content became 40 ppm, and a extraction of seaweed was further added to the feed so that the iodine content was 40 ppm. The feed was fed to hens in the same way as the example 1. Thus, the hens laid eggs containing on the average 650μg of monoiodohistidine per egg.

EXAMPLE 4

Sodium iodide was added to a marketed feed for hens so that the iodine content became 2,000 ppm, and then the feed was fed to hens in the same way as the example 1. Eggs which the hens laid were broken, and dextrin of 5 kg was added to the broken egg of 100 kg. The addmixture of broken egg and dextrin was dried by a freeze-drying apparatus. Then, the dried admixture was granulated by a fluid layers-granulater in parallel with adding 1% of gelatine thereto.

The composite obtained in such way contained monoiodohistidine of 220 mg/kg.

EXAMPLE 5

Potassium iodide was added to a marketed feed for hens so that the iodine content became 150 ppm, and then monoiodohistidine-enriched eggs were obtained in the same was as the example 1. The egg were broken in order to separate the yolk therefrom, and then the separated yolk was freeze-dried to make into the composite of the present invention.

We claim:

1. A method for increasing the constitution ratio of haematic high-density lipoprotein, increasing lipoprotein lipase activity, and decreasing plasma triglyceride, which comprises dosing humans with an egg product containing monoiodohistidine, wherein the amount of monoiodohistidine comprises 200 to 2,000 μg per day for at least a month.

2. The method according to claim 1, wherein the iodohistidine is present in iodine-enriched whole egg or egg yolk obtained by feeding an iodine-containing material selected from the group consisting of iodine-containing compounds and seaweed and mixtures thereof to egg-laying birds in excess of their ordinary iodine requirement.

3. The method according to claim 2, wherein the egg is in the form of granules, essence, tablet or powder.

* * * * *